(12) United States Patent
Hotta

(10) Patent No.: US 10,101,199 B2
(45) Date of Patent: Oct. 16, 2018

(54) INSPECTION APPARATUS

(71) Applicant: FUJI XEROX CO., LTD., Tokyo (JP)

(72) Inventor: Hiroyuki Hotta, Kanagawa (JP)

(73) Assignee: FUJI XEROX CO., LTD., Minato-ku, Tokyo (JP)

( * ) Notice: Subject to any disclaimer, the term of this patent is extended or adjusted under 35 U.S.C. 154(b) by 122 days.

(21) Appl. No.: 15/429,363

(22) Filed: Feb. 10, 2017

(65) Prior Publication Data

US 2017/0268925 A1    Sep. 21, 2017

(30) Foreign Application Priority Data

Mar. 18, 2016    (JP) .................................. 2016-055649

(51) Int. Cl.
| | | |
|---|---|---|
| *G01J 1/04* | (2006.01) | |
| *G01J 1/16* | (2006.01) | |
| *G01J 1/06* | (2006.01) | |
| *G01N 21/88* | (2006.01) | |

(52) U.S. Cl.
CPC .......... *G01J 1/1626* (2013.01); *G01J 1/0411* (2013.01); *G01J 1/06* (2013.01); *G01N 21/8806* (2013.01)

(58) Field of Classification Search
CPC ... G01B 21/8806; G01J 1/0411; G01J 1/0437; G01J 1/0455
USPC ...................................................... 356/237.1
See application file for complete search history.

(56) References Cited

U.S. PATENT DOCUMENTS

| | | | | |
|---|---|---|---|---|
| 8,203,710 | B1* | 6/2012 | Mitchell | ............... G01J 3/0208 |
| | | | | 356/328 |
| 2015/0116718 | A1 | 4/2015 | Ochi et al. | |
| 2015/0247798 | A1 | 9/2015 | Seki et al. | |
| 2017/0161544 | A1* | 6/2017 | Fomani | ............... G06K 9/0008 |

FOREIGN PATENT DOCUMENTS

| | | |
|---|---|---|
| JP | 2015-81892 A | 4/2015 |
| JP | 2015-161634 A | 9/2015 |

* cited by examiner

*Primary Examiner* — Tri Ton
*Assistant Examiner* — Rebecca C Bryant
(74) *Attorney, Agent, or Firm* — Sughrue Mion, PLLC

(57) ABSTRACT

An inspection apparatus includes a light emitting unit, a first lens, an aperture unit, a second lens, a light receiving unit, and an inspection unit. The light emitting unit emits irradiation light to an object to be inspected. The first lens changes a divergence level of the irradiation light which is emitted from the light emitting unit and is transmitted through the first lens. The aperture unit has an opening which narrows the irradiation light transmitted through the first lens. The second lens condenses the irradiation light passing through the opening, toward the object. The light receiving unit is disposed between the aperture unit and the second lens. The light receiving unit includes plural light receiving elements which receives reflected light obtained by the irradiation light being emitted to the object and then being transmitted through the second lens.

20 Claims, 21 Drawing Sheets

INSPECTION APPARATUS

CROSS-REFERENCE TO RELATED APPLICATIONS

This application is based on and claims priority under 35 USC 119 from Japanese Patent Application No. 2016-055649 filed Mar. 18, 2016.

BACKGROUND

Technical Field

The present invention relates to an inspection apparatus.

SUMMARY

According to an aspect of the invention, an inspection apparatus includes a light emitting unit, a first lens, an aperture unit, a second lens, a light receiving unit, and an inspection unit. The light emitting unit emits irradiation light to an object to be inspected. The first lens changes a divergence level of the irradiation light which is emitted from the light emitting unit and is transmitted through the first lens. The aperture unit has an opening which narrows the irradiation light transmitted through the first lens. The second lens condenses the irradiation light passing through the opening, toward the object. The light receiving unit is disposed between the aperture unit and the second lens. The light receiving unit includes plural light receiving elements which receives reflected light obtained by the irradiation light being emitted to the object and then being transmitted through the second lens. The plural light receiving elements are disposed so as not to overlap the opening. The inspection unit inspects respective inspection locations of the object using (i) light receiving results of the light receiving unit for the respective inspection locations of the object and (ii) a reference value.

BRIEF DESCRIPTION OF THE DRAWINGS

Exemplary embodiments of the present invention will be described in detail based on the following figures, wherein.

DETAILED DESCRIPTION

Figure 1:
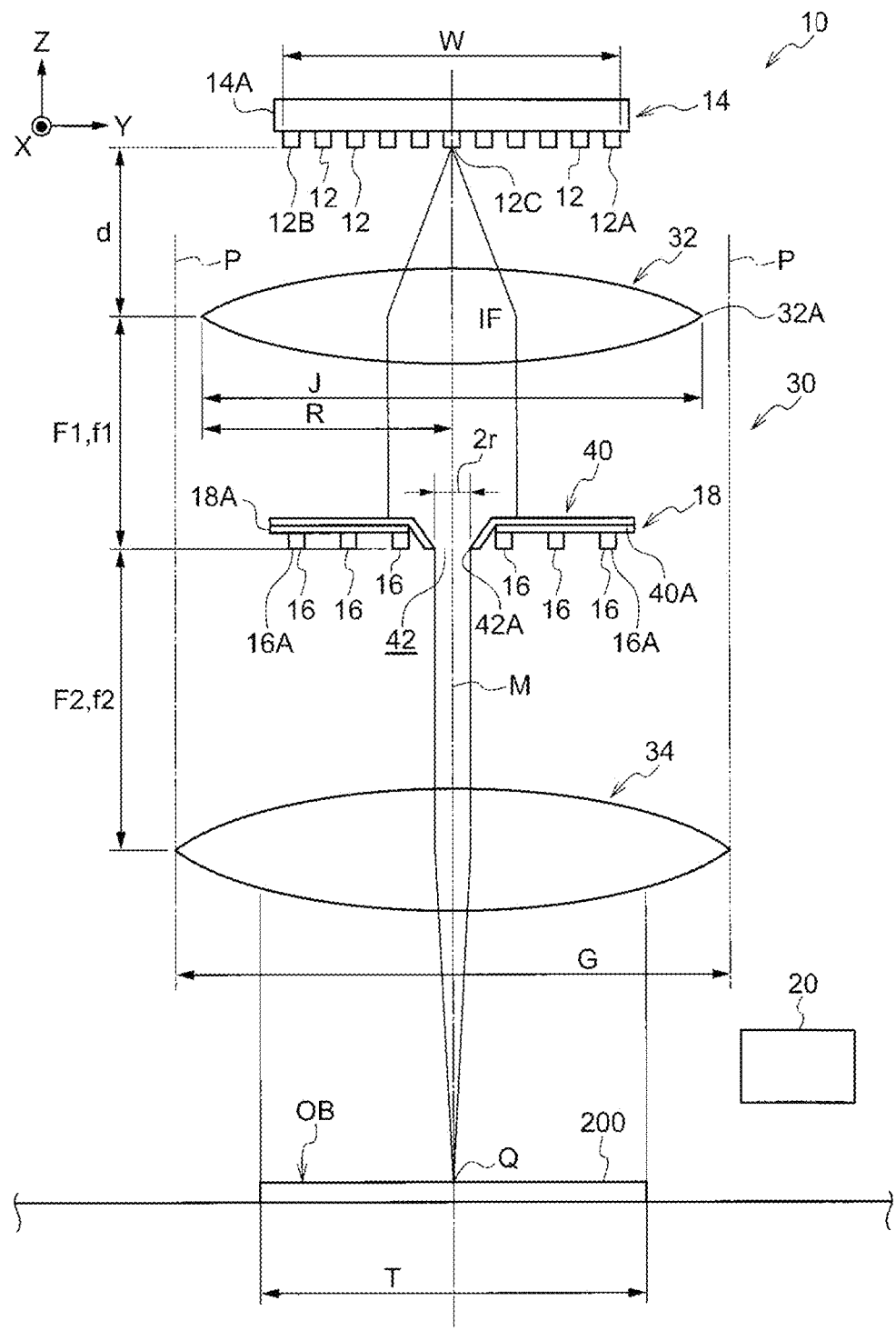
FIG. 1 is a schematic configuration diagram illustrating an inspection apparatus according to one exemplary embodiment of the present invention.

An example of an inspection apparatus according to one exemplary embodiment of the present invention will be described with reference to FIGS. 1 to 23. In the drawings, an arrow Z illustrates an up and down direction (in the present exemplary embodiment, a vertical direction) of an apparatus, an arrow Y indicates a width direction (in the present exemplary embodiment, a horizontal direction) of the apparatus, and an arrow X indicates a depth direction (in the present exemplary embodiment, a horizontal direction) of the apparatus which is orthogonal to the Y direction and the Z direction.

<Configuration>

The configuration of an inspection apparatus 10 will be described.

The inspection apparatus 10 illustrated in FIG. 1 is an apparatus for inspecting reflection characteristics of an object OB to be inspected by irradiating the object OB with light beams (light rays) when the object OB is moved in a depth direction (X direction) of the apparatus. In the present exemplary embodiment, the wording "reflection characteristics" means a distribution of intensity of light reflected in a single direction or plural directions due to a roughness level such as a small unevenness or an undulation of a surface of the object OB.

The inspection apparatus 10 includes a light emitting unit 14 having plural light emitting elements 12, a light receiving unit 18 (see FIG. 3) having plural light receiving elements 16, and a controller 20 as an example of an inspection unit. In addition, the inspection apparatus 10 is disposed between the light emitting unit 14 and the object OB to be inspected, and has an optical system 30 that guides irradiation light IF, which is emitted from the light emitting element 12, to the object OB.

[Light Emitting Unit]

As illustrated in FIG. 1, the light emitting unit 14 is disposed above an inspection region T in an up and down direction of the apparatus, and the object OB, which moves in the depth direction of the apparatus, passes through the inspection region T. In addition, the light emitting unit 14 has plural light emitting elements 12 which are mounted on a substrate 14A, are arranged in the width direction (Y direction) of the apparatus, and emit the light beams downward in the up and down direction (−Z direction) of the apparatus. As described above, the light emitting elements 12 are arranged in a direction intersecting with (orthogonal to) the movement direction of the object OB (the depth direction (X direction) of the apparatus).

The light emitting element 12, which is disposed at one end portion (a right end in the drawing) in the Y-axis direction of the substrate 14A, is referred to as a light emitting element 12A, the light emitting element 12, which is disposed at the other end portion (a left end in the drawing) in the Y-axis direction of the substrate 14A, is referred to as a light emitting element 12B, and the light emitting element 12, which is disposed at a center of the substrate 14A, is referred to as a light emitting element 12C.

The light beams are emitted from the respective light emitting elements 12 toward the object OB at a time interval from the light emitting element 12A disposed at one end portion (the right end in the drawing) in the width direction of the apparatus to the light emitting element 12B disposed at the other end portion (the left end in the drawing) in the width direction of the apparatus.

While the object OB moves in the −X direction in the inspection region T, a cycle of light emission from the light emitting element 12A to the light emitting element 12B is repeated several times.

Figure 2:
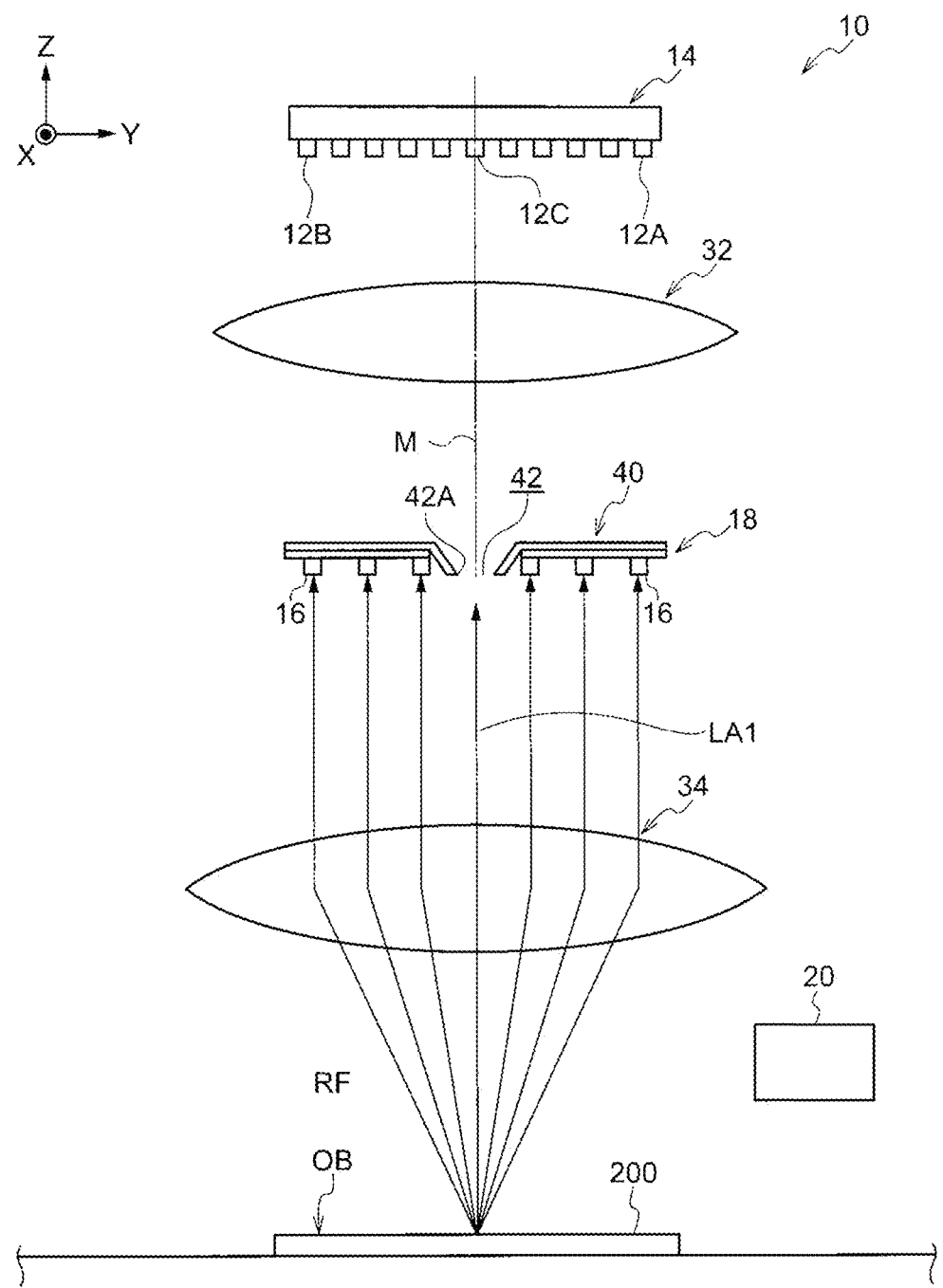
FIG. 2 is a schematic configuration diagram illustrating reflected light of the inspection apparatus in FIG. 1.

FIG. 1 illustrates the light beam of irradiation light IF when the light emitting element 12C emits light, and FIG. 2 illustrates the light beam of reflected light RF when the irradiation light IF emitted from the light emitting element 12C is reflected by a surface 200 of the object OB.

[Optical System]

The optical system 30 illustrated in FIG. 1 constitutes a so-called double-sided telecentric lens which includes a first lens 32, a second lens 34, and an aperture unit 40 which is disposed between the first lens 32 and the second lens 34 and narrows the light beam of the irradiation light IF.

Further, the optical system 30 is disposed between the light emitting unit 14 and the object OB, and configured to guide the irradiation light IF emitted from the light emitting element 12 to the object OB, and guide the reflected light RF (see FIG. 2) reflected by the object OB to the light receiving unit 18.

Figure 6A:
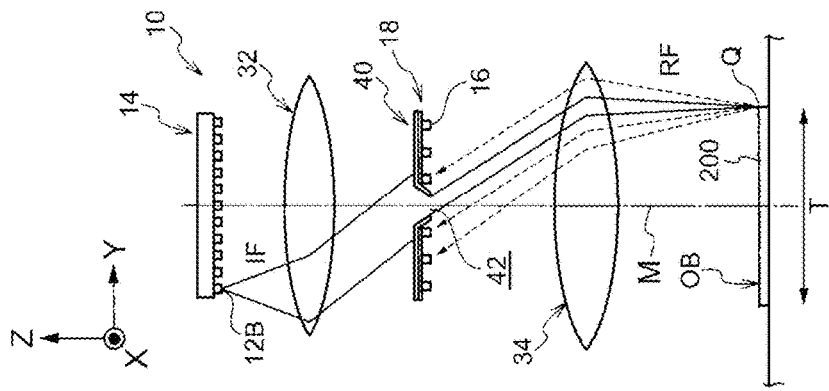
FIGS. 6A to 6C are process diagrams sequentially illustrating a process of inspecting an object to be inspected using the inspection apparatus in FIG. 1.
Figure 6B:
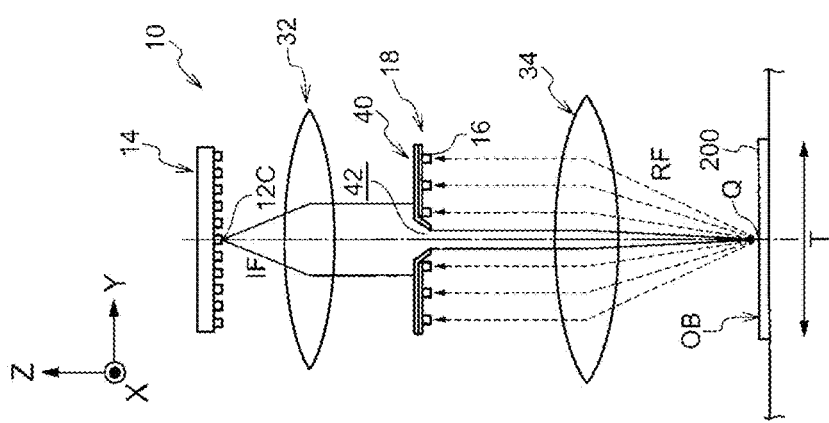
Figure 6C:
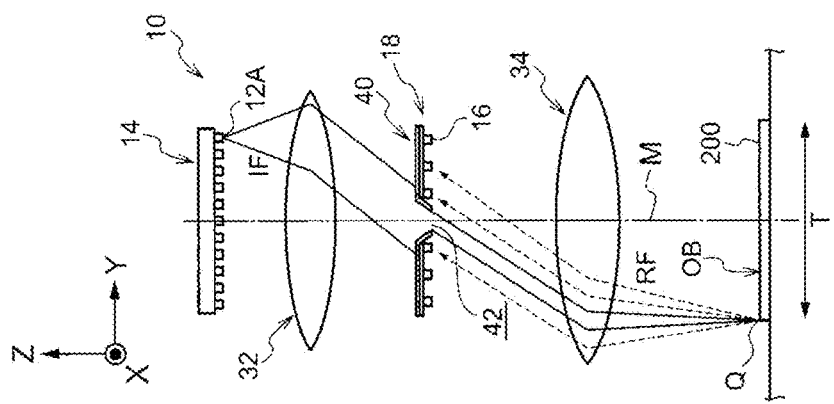

That is, as illustrated in FIGS. 1, 2, and 6, the light receiving unit 18 is configured to receive at least a part of the reflected light RF (see FIG. 2 and FIGS. 6A to 6C) generated when the irradiation light IF (see FIG. 1 and FIGS. 6A to 6C) from the light emitting element 12, which is emitted from the second lens 34, is reflected by the object OB, and then transmitted through the second lens 34 again.

As illustrated in FIG. 1, the first lens 32 and the second lens 34 are disposed such that an optical axis M of the first lens 32 and an optical axis M of the second lens 34 are coaxial with each other, and the optical axes M of the first lens 32 and the second lens 34 are directed in the up and down direction of the apparatus. In addition, in the light emitting element 12, the light emitting element 12C disposed at the center in the width direction of the apparatus is disposed on the optical axis M.

From another point of view, the first lens 32 and the second lens 34 have the same optical axis M, and the optical axis M passes through a center of the light emitting element 12C of the light emitting unit 14 and a center of an opening 42 which will be described later.

The first lens 32 is a circular convex lens in a plan view, and a dimension of the first lens 32 in the width direction of the apparatus (dimension J in the drawing) is configured to be greater than a dimension in the width direction of the apparatus from the light emitting element 12A to the light emitting element 12B (dimension W in the drawing). Therefore, as the light beams emitted from the respective light emitting elements 12 are transmitted through the first lens 32, a divergence level of the light beams transmitted through the first lens 32 is changed, so that the light beams are directed as parallel light toward the second lens 34.

The second lens 34 is a circular convex lens in a plan view, and a dimension of the second lens 34 in the width direction of the apparatus (dimension G in the drawing) is greater than a dimension of the first lens 32 in the width direction of the apparatus. Further, the second lens 34 is configured to condense the light beams, which is emitted from the first lens 32 and transmitted through the second lens 34, toward the object OB.

The aperture unit 40 is disposed between the first lens 32 and the second lens 34. Further, the circular opening 42 is formed in the aperture unit 40 to narrow the light beam which is transmitted through the first lens 32 and is incident on the second lens 34 (see FIG. 3).

More specifically, the aperture unit 40 has a plate shape in which the plate surface is directed in the up and down direction of the apparatus, an outer edge portion of the opening 42 of the aperture unit 40 is curved toward the second lens 34 and tapered, and a tip portion of the outer edge portion is formed as an opening edge 42A. In addition, a circular shape formed by the opening 42 has the optical axis M as a central axis thereof. Further, the light beam, which is emitted from the light emitting element 12, is transmitted through the first lens 32, and is incident on the second lens 34, is narrowed by the opening 42.

In the Z-axis direction (optical axis M direction), a distance F1 between the opening edge 42A and the first lens 32 is configured to be equal or substantially equal to a focal length f1 of the first lens 32. In addition, in the Z-axis direction (optical axis M direction), a distance F2 between the opening edge 42A and the second lens 34 is equal or substantially equal to a focal length f2 of the second lens 34.

In the optical system 30 according to the present exemplary embodiment configured as described above, the light beams, which are sequentially emitted from the respective light emitting elements 12, are thinly narrowed, regardless of the positions of the light emitting elements 12, and are also irradiated to the object OB as the irradiation light IF parallel to the optical axis M. In other words, the respective light emitting elements 12 are caused to sequentially emit and scan such that the object OB is sequentially irradiated with substantially circular light beams which are thinly narrowed and parallel to each other (see FIGS. 6A to 6C).

[Light Receiving Unit]

As illustrated in FIG. 1, the light receiving unit 18 has plural light receiving elements 16 which are disposed between the first lens 32 and the second lens 34 at a back surface side 40A of the aperture unit 40 (the second lens 34 side, a lower side in the up and down direction of the apparatus), and are mounted on a substrate 18A.

Figure 3:
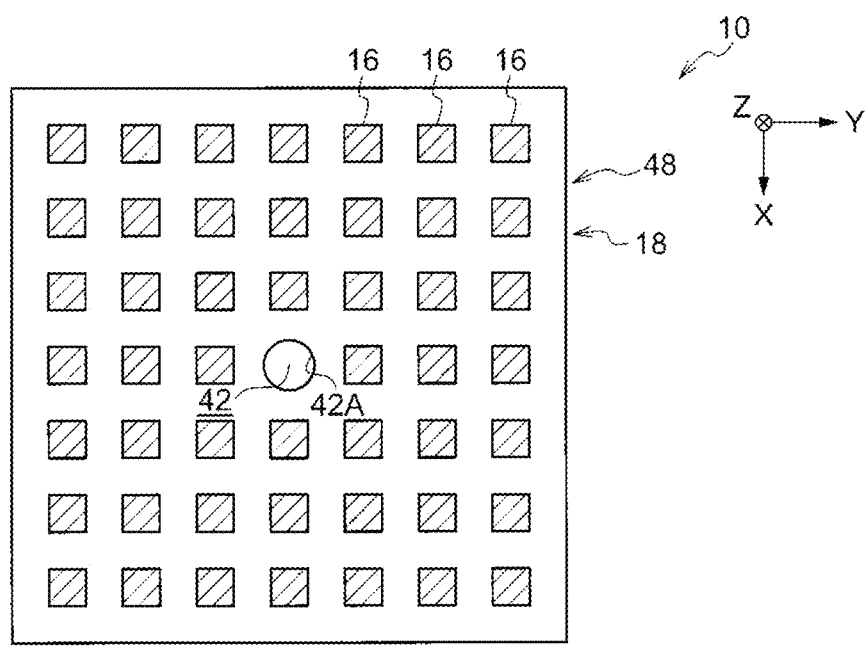
FIG. 3 is a top plan view illustrating an example of the arrangement of light receiving elements of a light receiving unit of the inspection apparatus in FIG. 1.

As illustrated in FIG. 3, the plural light receiving elements 16 are disposed at intervals in the width direction of the apparatus and in the depth direction of the apparatus, except for the opening 42 of the aperture unit 40.

As illustrated in FIG. 2, the light receiving elements 16 are disposed between the first lens 32 and the second lens 34, and receive at least a part of the reflected light RF which is reflected by the object OB and transmitted through the second lens 34 of the optical system 30.

In the present exemplary embodiment, as illustrated in FIG. 1, the light receiving elements 16 are disposed at an optical axis M side (at an inner side) of a line P (cylindrical surface) in the width direction of the apparatus. The line P extends in the up and down direction of the apparatus while passing through an outer diameter end (a virtual contact point between a front surface Rd (radius) and a back surface Rd) of one lens (in the present exemplary embodiment, the second lens 34) having a larger outer diameter than the other lens (in the present exemplary embodiment, the first lens 32) has. If plural Rds are present in the front surface Rd or the back surface Rd, the outer diameter end is determined using the Rd having the largest value.

In the Z-axis direction (optical axis M direction), a height position of a light receiving surface A of each of the light receiving elements 16 is configured to be equal or substantially equal to a height position of the opening edge 42A. In addition, in the Z-axis direction (optical axis M direction), a distance (optical path length: F2 in the drawing) between a light receiving surface 16A of each of the light receiving elements 16 and the second lens 34 is configured to be equal or substantially equal to the focal length f2 of the second lens 34.

Since the light receiving element 16 cannot be disposed at a position of the opening 42, a pitch in the light receiving unit 18 between the light receiving element 16 disposed at the left end in the drawing and the light receiving element 16 disposed at the right end in the drawing is greater than a pitch between the other light receiving elements 16. In other words, the light receiving element 16 to be disposed at a central portion of the light receiving unit 18 is omitted (see FIG. 3).

[Controller]

Figure 4:
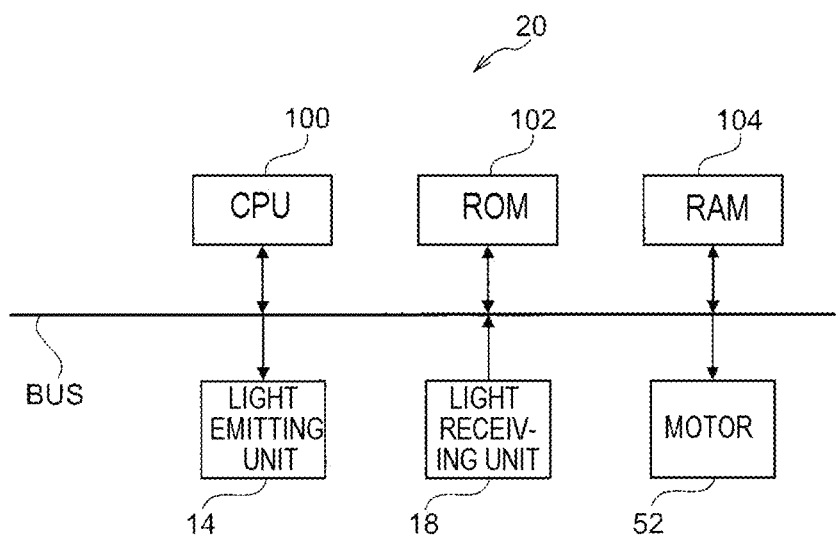
FIG. 4 is a block diagram of a controller of the inspection apparatus in FIG. 1.

As illustrated in FIG. 4, the controller 20, as an example of the inspection unit, includes a central processing unit (CPU) 100, a read only memory (ROM) 102, a random access memory (RAM) 104, and the like.

The CPU 100 collectively controls the entire inspection apparatus 10, the ROM 102 is a memory that stores in advance a control program or the like for the inspection apparatus 10, and the RAM 104 is a memory which is used as a work area when a program such as the control program is executed. The CPU 100, the ROM 102, and the RAM 104 are connected with each other by a bus.

A motor 52 for driving the light emitting unit 14, the light receiving unit 18, and the like is connected to the bus, and the light emitting unit 14, the light receiving unit 18, and the motor 52 are each controlled by the CPU 100 through the bus.

Figure 5:
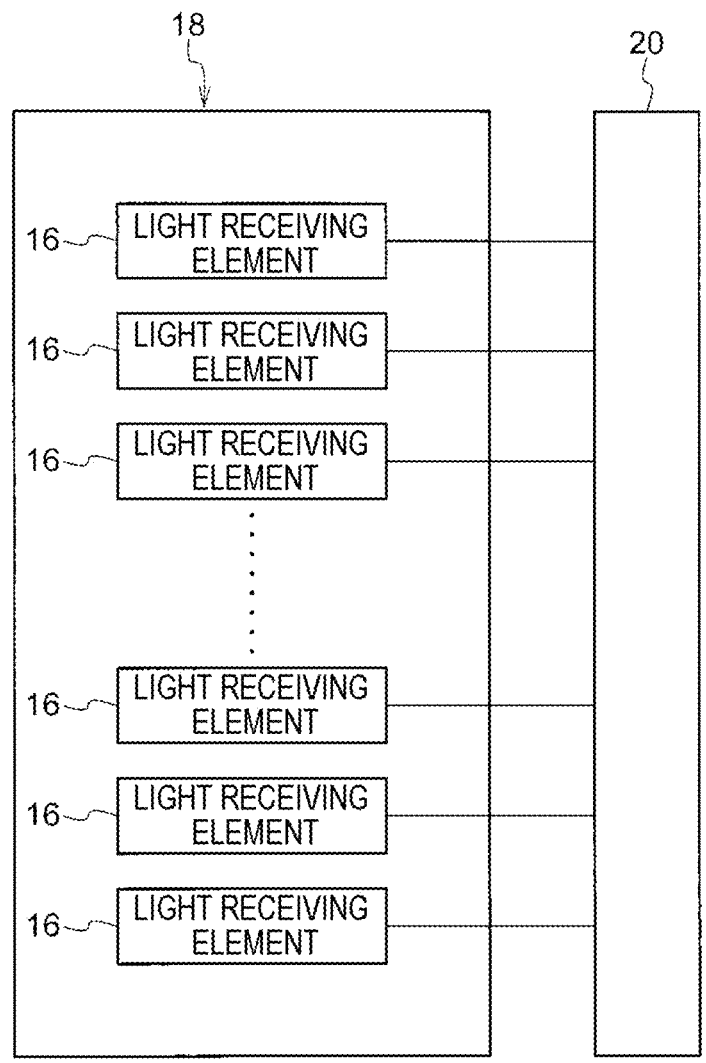
FIG. 5 is a block diagram of the controller and the light receiving unit of the inspection apparatus in FIG. 1.

As illustrated in FIG. 5, the controller 20 receives a light receiving result of the plural light receiving elements 16, and inspects the reflection characteristics of the object OB using the light receiving result of the plural light receiving elements 16.

(Overview of Inspection Method)

Next, an overview of the method of inspecting the reflection characteristics of the surface 200 of the object OB to be inspected by the controller 20 will be described.

FIGS. 6A to 6C illustrate the light beam of the irradiation light IF, and the light beam of the reflected light RF in which the irradiation light IF is reflected by the surface 200 of the object OB and guided to the light receiving unit 18, in a case where the light emitting elements 12A, 12C, and 12B of the light emitting unit 14 sequentially emit light.

First, when the object OB moves in the −X direction, and a tip of the object OB enters the inspection region T, the respective light emitting elements 12 sequentially emit light at time intervals, and the irradiation light IF is sequentially emitted toward the object OB. Further, until a rear end of the object OB exits the inspection region T, a cycle of light emission from the light emitting element 12A to the light emitting element 12B is repeated. As described above, the light emission of the light emitting elements 12 is controlled by the controller 20.

A divergence level of the light beam of the irradiation light IF emitted from the respective light emitting elements 12 is changed by the first lens 32 so that the light beam is directed toward the second lens 34. The light beam of which the divergence level is changed by the first lens 32 is narrowed (restricted) by the opening 42 of the aperture unit 40. The light beam narrowed by the aperture unit 40 is condensed by the second lens 34, and emitted to the object OB from the Z-axis direction (the direction parallel to the optical axis M). The surface 200 of the object OB is configured to pass through a portion in the vicinity of a condensing point Q of the irradiation light IF by the second lens 34.

The irradiation light IF emitted to the object OB is reflected by the surface 200 of the object OB, thereby generating the reflected light RF (indicated by a dashed-dotted line with an arrow in FIGS. 6A to 6C). The direction of the light beam of the reflected light RF is changed by the second lens 34 so that the light beam is directed toward the respective light receiving elements 16. The reflected light RF transmitted through the second lens 34 is received by the respective light receiving elements 16.

In accordance with the state of the surface 200 of the object OB, the irradiation light IF is reflected in various directions. The respective light receiving elements 16 output light receiving signals based on the amount of received light. The light receiving signal is read at a predetermined timing by control of the controller 20. The light receiving signal may be temporarily stored in the memory such as the RAM 104. The controller 20 inspects the surface 200 of the object OB by using an inspection method which will be described later.

As illustrated in FIG. 2, light LA1 specularly reflected by a central portion of the surface 200 of the object OB in the width direction of the apparatus is transmitted through the second lens 34, and then passes through the opening 42 of the aperture unit 40. As a result, the specularly reflected light LA1 is not received by the light receiving element 16. In other words, the specularly reflected light LA1 from the central portion is not received.

Here, as an example, a method of inspecting, by the controller 20, two types of surfaces 200A and 200B having different roughness levels that have an effect on the reflection characteristics of the surface 200 of the object OB will be described.

Figure 7A:
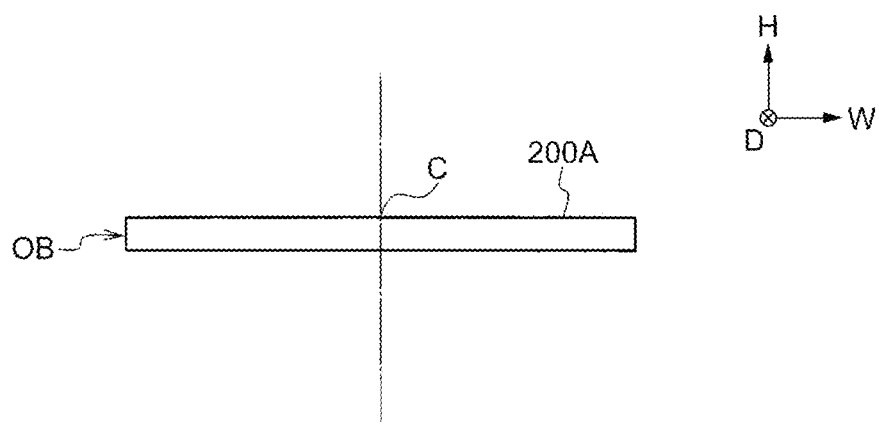
FIG. 7A is a side view illustrating an object to be inspected.
Figure 7B:
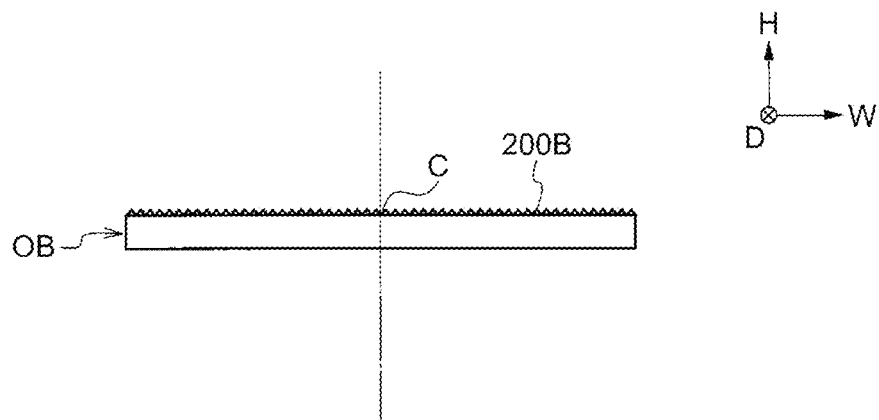
FIG. 7B is a side view illustrating an object having a higher unevenness level than that of the object in FIG. 7A.

As illustrated in FIGS. 7A and 7B, the surface 200A (FIG. 7A) has a lower roughness level than that of the surface 200B (FIG. 7B). In addition, the vertical axis in the graphs illustrated in FIGS. 8A and 8B indicates the magnitude of the light amount of the reflected light RF received by the respective light receiving elements 16.

Figure 8A:
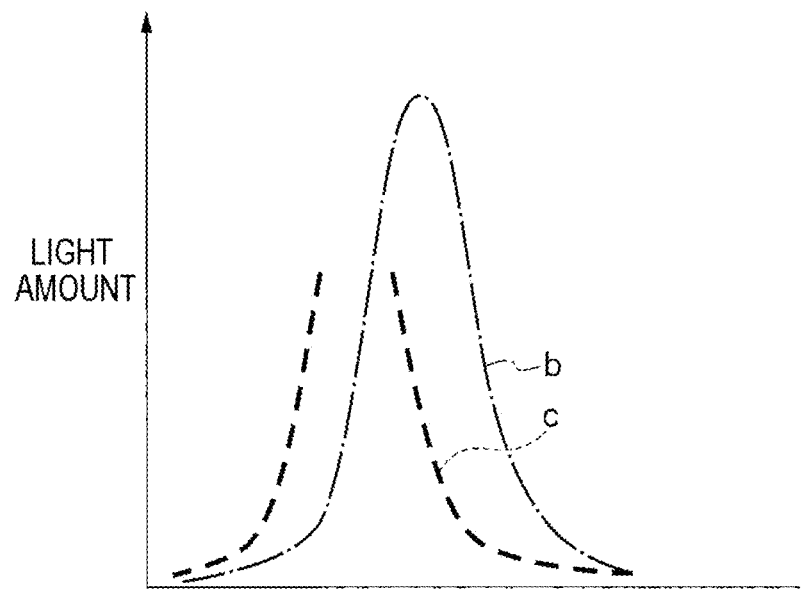
FIG. 8A is a graph illustrating an inspection result of the object in FIG. 7A.

As illustrated in FIG. 8A, in the case of the surface 200A having a low roughness level as illustrated in FIG. 7A, the light amount of the specularly reflected light (hereinafter, referred to as "specular reflection component") is larger than the light amount of the diffuse reflection light (hereinafter, referred to as a "diffuse reflection component"), and as a result, a steep curve is plotted. Meanwhile, as illustrated in FIG. 8B, in the case of the surface 200B having a high roughness level as illustrated in FIG. 8B, a difference between the specular reflection component and the diffuse reflection component is reduced in comparison with the surface 200A, and as a result, a gentle curve is plotted.

Figure 12:
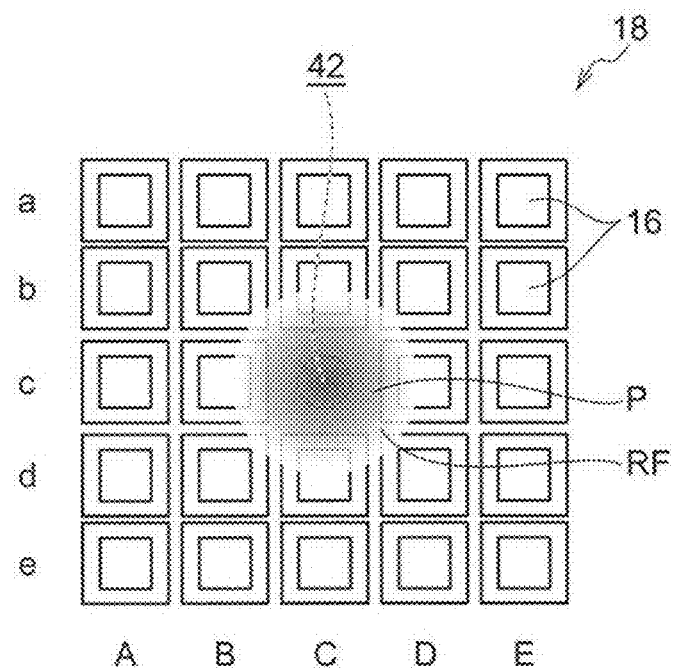
FIG. 12 is a top plan view of the light receiving unit, which illustrates an example in which a peak of specularly reflected light is directed toward an opening of the light receiving unit.
Figure 17:
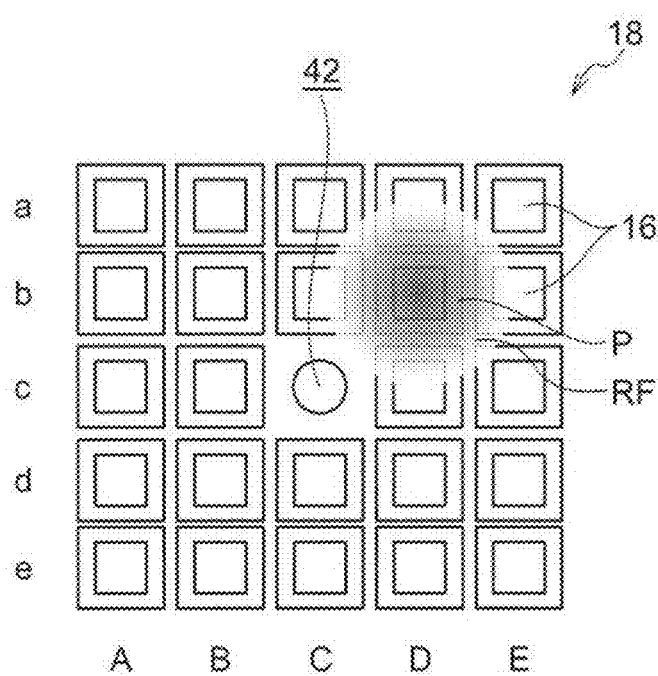
FIG. 17 is a top plan view of the light receiving unit, which illustrates an example in which a peak of specularly reflected light is directed toward a portion other than the opening of the light receiving unit.
Figure 18:
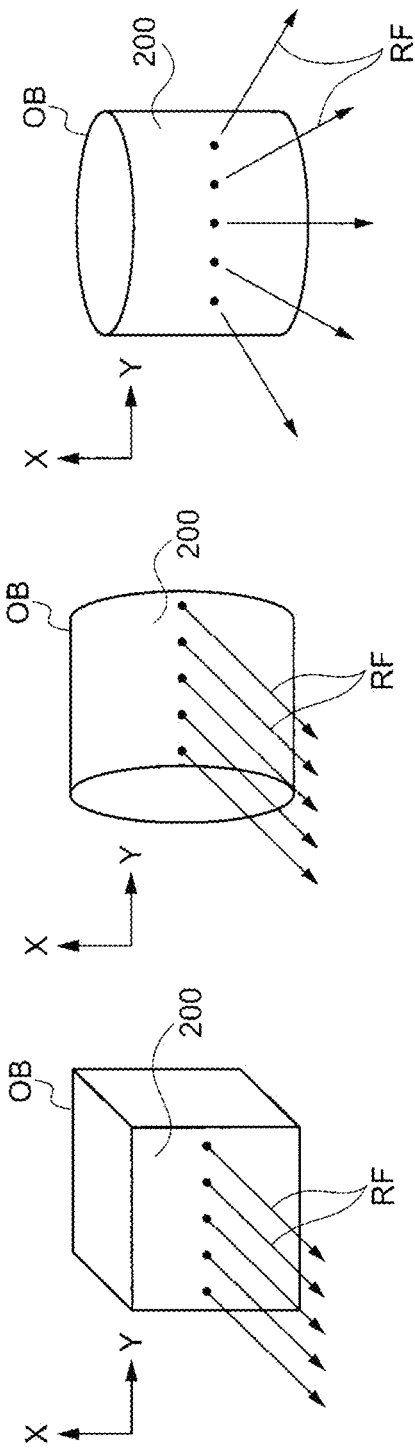
FIGS. 18A and 18B are explanatory views illustrating an example in which a direction of reflected light is a straight direction.
FIG. 18C is an explanatory view illustrating an example in which a direction of reflected light is a curved direction.

A distribution c in FIG. 8A indicates the light amount of the light receiving elements 16 in a row c, in a case where a peak P of the specularly reflected light of the reflected light RF is directed toward a position Cc (opening 42) as illustrated in FIG. 12 which will be described later. In addition, a distribution b indicates the light amount of the light receiving elements 16 in a row b in a case where a peak P of the specularly reflected light of the reflected light RF is directed toward a position Db as illustrated in FIG. 17 which will be described later.

Figure 8B:
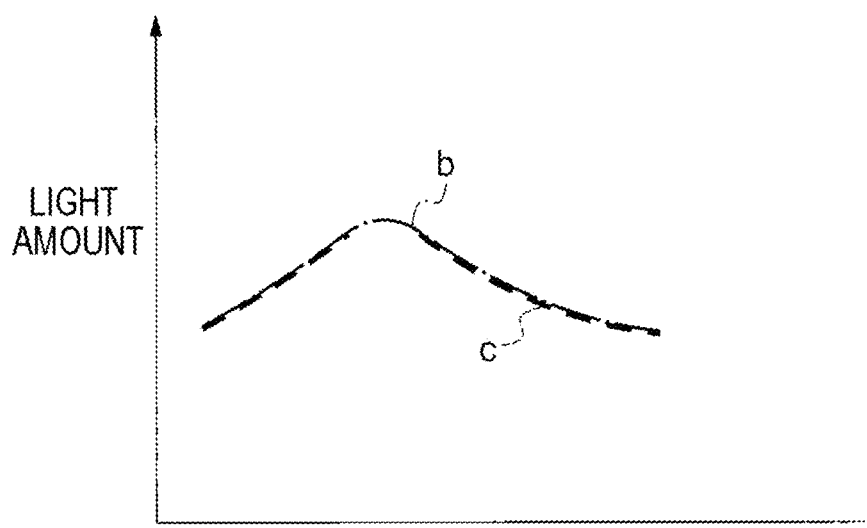
FIG. 8B is a graph illustrating an inspection result of the object in FIG. 7B.

In FIG. 8B, the distribution c indicates the light amount of the light receiving elements 16 in the row c, and the distribution b indicates the light amount of the light receiving elements 16 in the row b.

<Detail of Inspection Method>

Next, a method of inspecting states of respective minute inspection locations of the surface 200 of the object OB to be inspected by the controller 20 will be described in detail. Further, respective inspection conditions (e.g., a state of the surface 200 or a position of the peak P of the specularly reflected light which is determined to be normal or abnormal) which will be described later are set in advance based on the object OB or the inspection contents, and then stored in the controller 20.

In the following description, a "median value" refers to a value which is positioned at a center when a limited number of data are arranged in descending order. In addition, in a case where the number of data is even, the median value is an arithmetic average value of two data close to the center.

Figure 9:
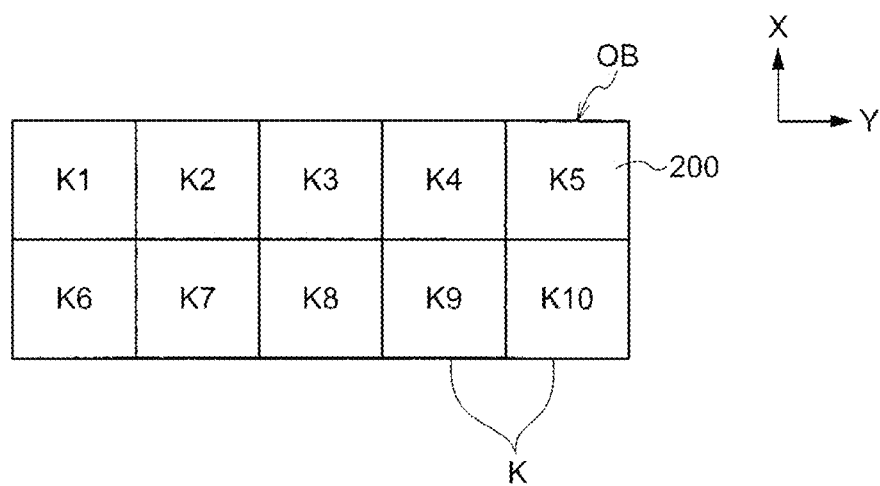
FIG. 9 is a top plan view for explaining a location for inspecting the object.

Further, FIG. 9 is a top plan view of the surface 200 of the object OB when viewed in the Z direction. As described above, the respective actual inspection locations are minute regions of the surface 200 of the object OB. To facilitate understanding, in the description on the present inspection method, it is assumed that the inspection locations are indicated by inspection locations K1 to K10 illustrated in FIG. 9. In a case where it is not necessary to distinguish the inspection locations K1 to K10, the inspection location may be referred to as an inspection location(s) K. In addition, the inspection location K illustrated in FIG. 9 is illustrative, and the present invention is not limited thereto.

Figure 10:
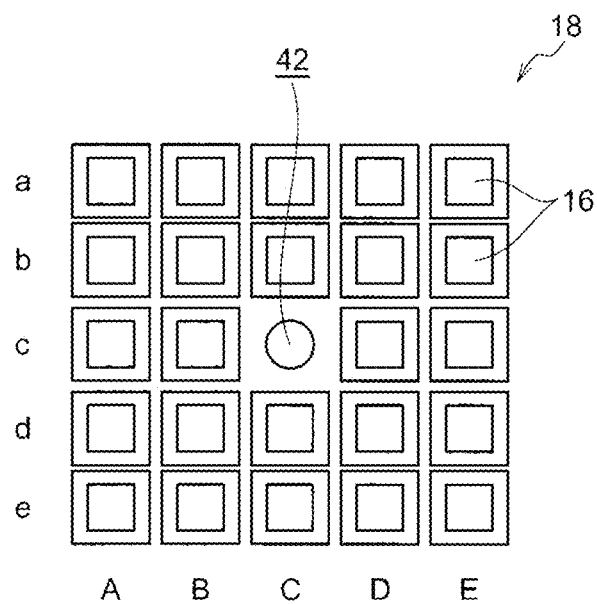
FIG. 10 is a top plan view of the light receiving unit, which illustrates an example of the arrangement of the light receiving elements.

In the description on the present inspection method, it is assumed that the light receiving elements 16 of the light receiving unit 18 are arranged as illustrated in FIG. 10. Further, for example, in a case of indicating a position of an edge portion at an upper right side in FIG. 10, it is denoted as a position Ea. In addition, the light receiving element 16 disposed at the position Ea is denoted as a light receiving element 16Ea. The respective light receiving elements 16 output signals proportional to the light amount of the received reflected light RF.

(First Inspection)

In the respective inspection locations K of the surface 200 of the object OB, a state (see FIGS. 7A and 8A) where the surface is a mirror surface having a low roughness level and the light amount (specular reflection component) of the specularly reflected light of the reflected light is large as illustrated in FIG. 7A is defined as "Normality", a state where the surface has scratches or a large unevenness and a direction of the specular reflection is changed is defined as "Abnormality A", and a state where the surface has a high roughness level and the light amount (diffuse reflection component) of the diffuse reflection light of the reflected light is large is defined as "Abnormality B". Further, description will be given on the first inspection for inspecting if an inspection location K is "Normality", "Abnormality A", or "Abnormality B".

First, description will be given on a case where an inspection location K on the surface 200 of the object OB is "Normality" and the specularly reflected light from the inspection location K is directed toward the position Cc (opening 42 (see FIG. 2, FIGS. 6A to 6C, and FIG. 12)).

[Abnormality A]

Figure 11:
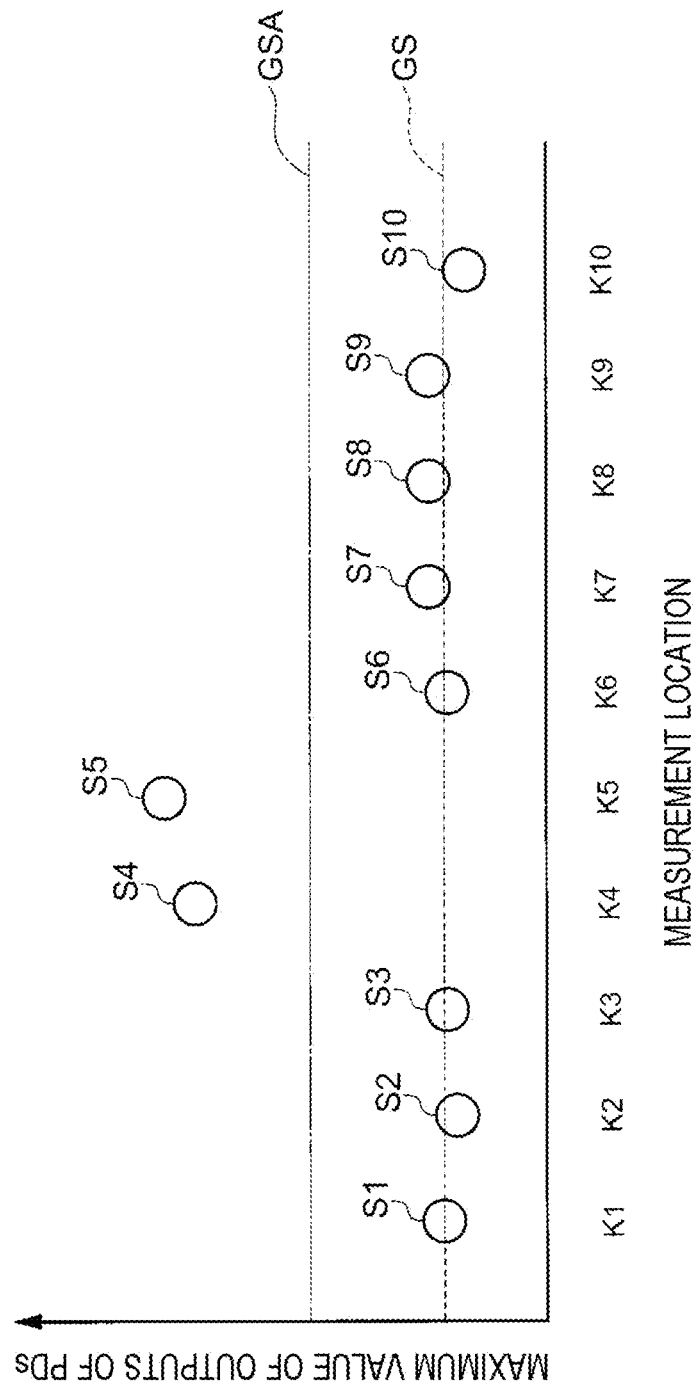
FIG. 11 is a graph for explaining an inspection for Abnormality A in a first inspection.

As illustrated in FIG. 11, the largest value, that is, the maximum value is obtained among output values (output proportional to the light amount of the received reflected light RF) of the plural light receiving elements 16 (see FIG. 10) for each inspection location K (see FIG. 9) on the surface 200 of the object OB. Next, a median value GS of the maximum values S1 to S10 of the plural inspection locations K is obtained, and the median value GS of the maximum values S1 to S10 is set to a reference value. Further, whether each inspection location K is "Normality" or "Abnormality A" is inspected using the maximum values S1 to S10 of the respective inspection locations K and the reference values (median value) GS.

Here, a case where the inspection location K4 and the inspection location K5 are Abnormality A as illustrated in FIG. 11 will be described.

As illustrated in FIG. 12, the specularly reflected light of the reflected light RF at the inspection locations K1 to K3 and K6 to K10 other than the inspection locations K4 and K5 is directed toward the opening 42. Since no light receiving element 16 is provided at the position Cc where the peak P of the light beam is present, the maximum value of the plural light receiving elements 16 is small (see the distribution c in FIG. 8A).

Figure 13:
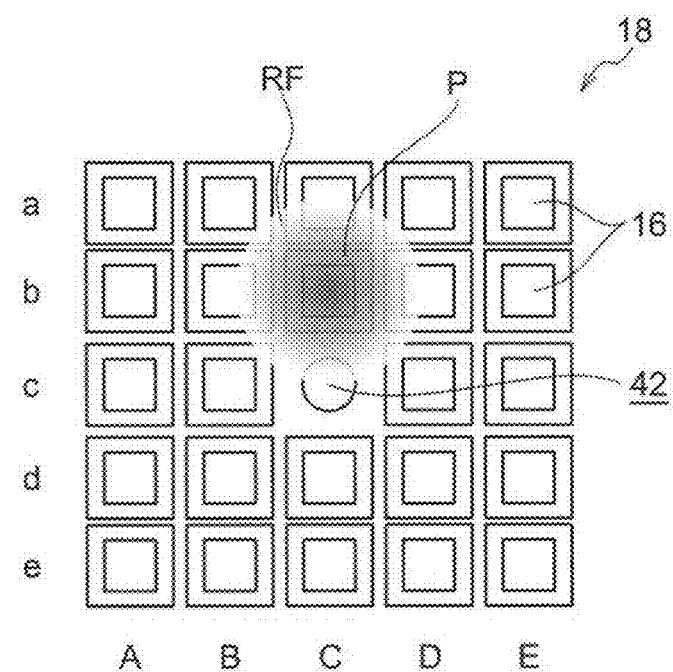
FIG. 13 is a top plan view of the light receiving unit, which illustrates an example in which a peak of specularly reflected light is directed toward a portion other than the opening of the light receiving unit.

In contrast, the direction of the specular reflection at the inspection locations K4 and K5 is different from that at the inspection locations K1 to K3 and K6 to K10. As illustrated in FIG. 13, the specularly reflected light of the reflected light RF from the inspection locations K4 and K5 is directed toward the position Cb instead of the opening 42. Therefore, the peak P of the light amount of the light beam is received by the light receiving element Cb, and the maximum value (in this example, an output value of the light receiving element 16Cb) of the plural light receiving elements 16 is large (see the distribution b in FIG. 8A).

Therefore, as illustrated in the graph in FIG. 11, the maximum values S4 and S5 in the inspection locations K4 and K5 protrude and increase. Further, the controller 20 determines whether the inspection location K is "Normality" or "Abnormality A," using the reference value (median value) GS and the maximum values S1 to S10.

For example, in a case where a difference between the reference value (median value) GS and each of the maximum values S1 to S10 is out of a predetermined range, the inspection location K is determined as "Abnormality A". Alternatively, a threshold value GSA is set by performing the four arithmetical operations on the reference value GS with a predetermined value, and the inspection location K having the maximum values S1 to S10 which exceed the threshold value GSA is determined as "Abnormality A".

[Abnormality B]

Figure 14:
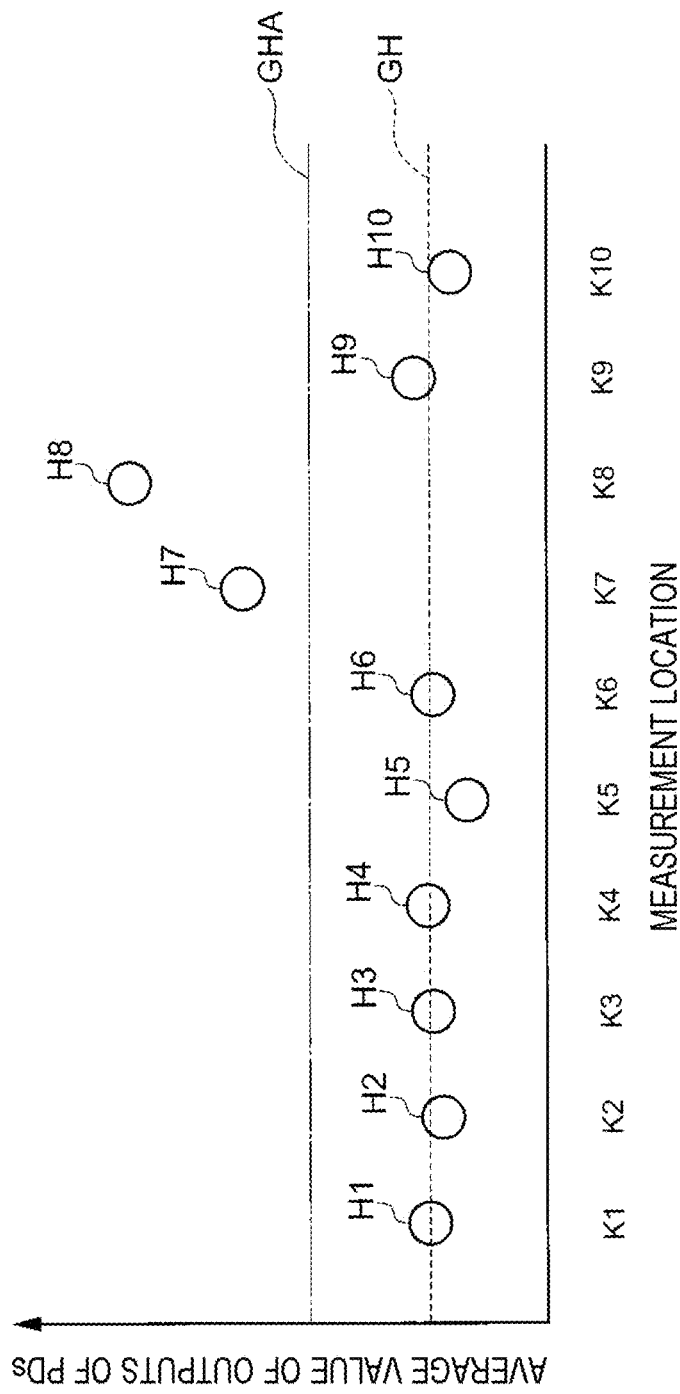
FIG. 14 is a graph for explaining an inspection for Abnormality B in the first inspection.

As illustrated in FIG. 14, an average value of the output values of the plural light receiving elements 16 (see FIG. 10) is obtained for each inspection location K (see FIG. 9) of the surface 200 of the object OB. Next, a median value GH of the average values H1 to H10 in the plural inspection locations K is obtained, and the median value GH of the average values H1 to H10 is set to the reference value. Further, whether each inspection location K is "Normality" or "Abnormality B" is inspected using the average values H1 to H10 of the respective inspection locations K and the reference value (median value) GH.

Here, a case where the inspection location K7 and the inspection location K8 are Abnormality B as illustrated in FIG. 14 will be described.

As illustrated in FIG. 12, the specularly reflected light of the reflected light RF from the inspection locations K1 to K6, K9, and K10 other than the inspection locations K7 and K8 is directed toward the opening 42 (position Cc). No light receiving element 16 is provided at the position Cc where the peak P of the light beam is present. Further, since a large number of specular reflection components of the reflected light RF are directed toward the opening 42, the light amount, which is received by the respective light receiving elements 16 disposed at positions other than the position of the opening 42 (position Cc), is small. Therefore, an average value of the output values of the plural light receiving elements 16 is small.

Figure 15:
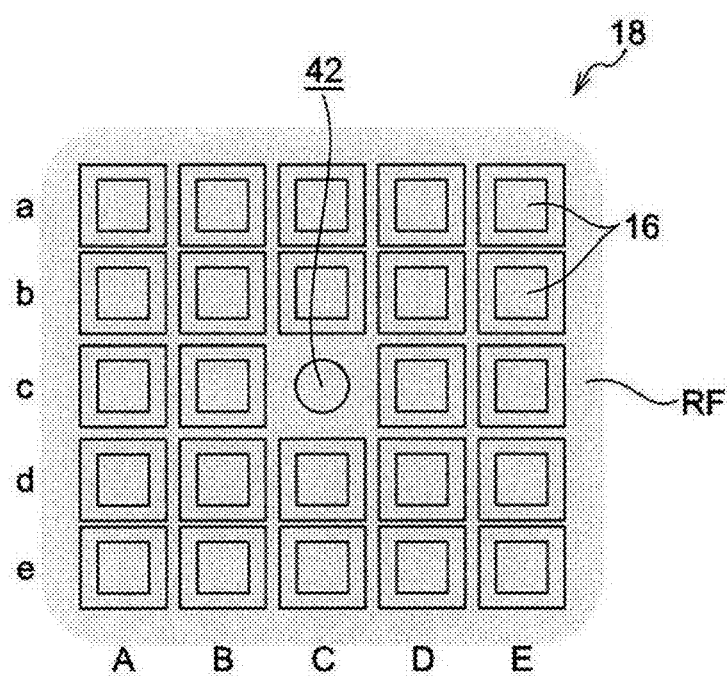
FIG. 15 is a top plan view illustrating an example in which the light receiving unit receives diffuse reflection light.

In contrast, in the inspection locations K7 and K8, as illustrated in FIG. 15, since a large number of diffuse reflection components of the reflected light RF are not directed toward the opening 42, the light amount, which is received by the respective light receiving elements 16 disposed at the positions other than the opening 42 (position Cc), is large. Therefore, an average value of the plural light receiving elements 16 is large.

Therefore, as illustrated in the graph in FIG. 14, the average values H7 and H8 in the inspection locations K7 and K8 protrude and increase. Further, the controller 20 determines whether the inspection location K is "Normality" or "Abnormality B," using the reference value (median value) GH and the average values H1 to H10.

For example, in a case where a difference between the reference value (median value) GH and each of the average values H1 to H10 is out of the predetermined range, the inspection location K is determined as "Abnormality A". Alternatively, a threshold value GHA is set by performing the four arithmetical operations on the reference value GH with a predetermined value, and the inspection location K having the average values H1 to H10 which exceed the threshold value GHA is determined as "Abnormality B".

Here, it can be said that when the average value H of the respective inspection locations K is large, the number of diffuse reflection components is large, that is, a roughness level is high, but when the average value H is small, the number of diffuse reflection components is small, that is, a roughness level is low. Therefore, in addition to the determination whether the inspection location is "Normality" or "Abnormality B," the roughness level may be determined based on the magnitude of the average value H.

In FIG. 14, since the average value H8 of the inspection location K8 is greater than the average value H7 of the inspection location K7, the roughness level of the inspection location K8 is higher than the roughness level of the inspection location K7.

Next, a case where the specularly reflected light is directed toward a portion other than the opening 42 when the reflected light RF of the inspection location K of the surface 200 of the object OB is "Normality" will be described.

In this case, an output value of the light receiving element 16 disposed at a position of the peak P of the reflected light RF, or output values of the light receiving element 16 and the peripheral light receiving elements 16 are not used. Further, whether each inspection location K is "Normality", "Abnormality A", or "Abnormality B" is inspected by the inspection method in the same manner as described above. Also, the roughness level of each inspection location K is inspected by the inspection method in the same manner as described above.

For example, in a case where the peak P of the reflected light RF appears at a position Db as illustrated in FIG. 17, an output value of the light receiving elements 16Db disposed at the position Db (or the light receiving element 16Db, and all or a part of the peripheral light receiving elements 16Cb, 16Ca, 16Da, 16Ea, 16Fb, 16Ec, and 16Dc) is not used. Further, whether each inspection location K is "Normality", "Abnormality A", or "Abnormality B" is inspected by the same method as the first inspection method. Also, the roughness level of each inspection location K is inspected by the same method as the first inspection method.

Even in a case where the reflected light RF is directed toward the opening 42 (position Cc) as described above, output values of all or a part of the light receiving elements 16Bb, 16Cb, 16Db, 16Dc, 16Cd, 16Bd, and 16Bc around the opening 42 (position Cc), may not be used.

Next, a case where the direction of the spectacularly reflected light of the reflected light RF from each of the inspection locations K which are "Normality" has a line shape instead of a dot shape will be described.

In a case where the surface 200 is a flat surface as illustrated in FIG. 18A, the specularly reflected light of the reflected light RF returns in the same direction. As a result, as illustrated in FIGS. 12 and 17, the peak P of the specularly reflected light of the reflected light RF has a dot shape.

Further, as illustrated in FIG. 18B, in a case where the scanning direction of the irradiation light IF (see FIGS. 6A to 6C), that is, the Y direction has a straight line shape, the specularly reflected light of the reflected light RF returns in the same direction even though the surface 200 is curved in the X direction. As a result, as illustrated in FIGS. 12 and 17, the peak P of the specularly reflected light of the reflected light RF has a dot shape.

However, as illustrated in FIG. 18C, in a case where the surface 200 is curved in the scanning direction (see FIGS.

6A to 6C) of the irradiation light IF, that is, in the Y direction, the specularly reflected light of the reflected light RF returns in a fan shape manner. As a result, as illustrated in FIG. 19, the peak P of the specularly reflected light of the reflected light RF has a line shape (accurately, the peaks P are arranged at an interval in the Y direction).

Figure 19:
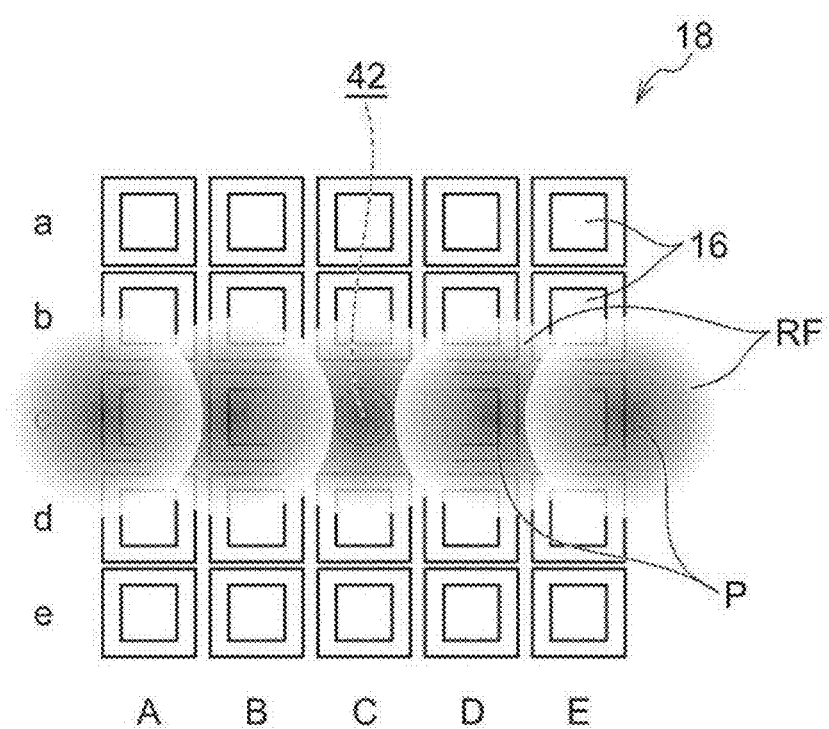
FIG. 19 is a top plan view of the light receiving unit, which illustrates a position of a peak of the specularly reflected light in a case where the direction of the reflected light in FIG. 18C is a curved direction.

Therefore, in the case illustrated in FIG. 19, output values of the light receiving elements 16Ac, 16Bc, 16Dc, and 16Ec (or including the light receiving elements 16 therearound) are not used. Further, whether each inspection location K is "Normality", "Abnormality A", "Abnormality B" is inspected by the same inspection method as described above. Also, the roughness level of each inspection location K is inspected by the same inspection method as described above.

In the case described so far, in a case where an unused light receiving element 16 is known in advance, the light receiving element 16 may not be installed in advance at the position where the light receiving element 16 is not used. In addition, felt or an anti-reflective structure such as coating may be provided at the position where the light receiving element 16 is not installed.

(Second Inspection)

Next, in the respective inspection locations K of the surface 200 of the object OB, a state (see FIGS. 7B and 8B) where a roughness level is high and the light amount (diffuse reflection component) of the diffuse reflection light of the reflected light is large is defined as "Normality", a state where a roughness level is low, the surface is a mirror surface, and the light amount (specular reflection component) of the specular reflection of the reflected light is large is defined as "Abnormality C", and a state where the surface has scratches or an unevenness and the direction of the specular reflection is changed is defined as "Abnormality D". Further, the second inspection for inspecting if an inspection location K is "Normality", "Abnormality C", or "Abnormality D" will be described.

"Normality" in the first inspection corresponds to "Abnormality C" in the second inspection, "Abnormality B" in the first inspection corresponds to "Abnormality D" in the second inspection, and "Abnormality B" in the first inspection corresponds to "Normality" in the second inspection.

First, a case where the specularly reflected light of the reflected light from the inspection location K which is on the surface 200 of the object OB and which is "Abnormality C" is directed toward the opening 42 will be described.

[Abnormality C]

Figure 22:
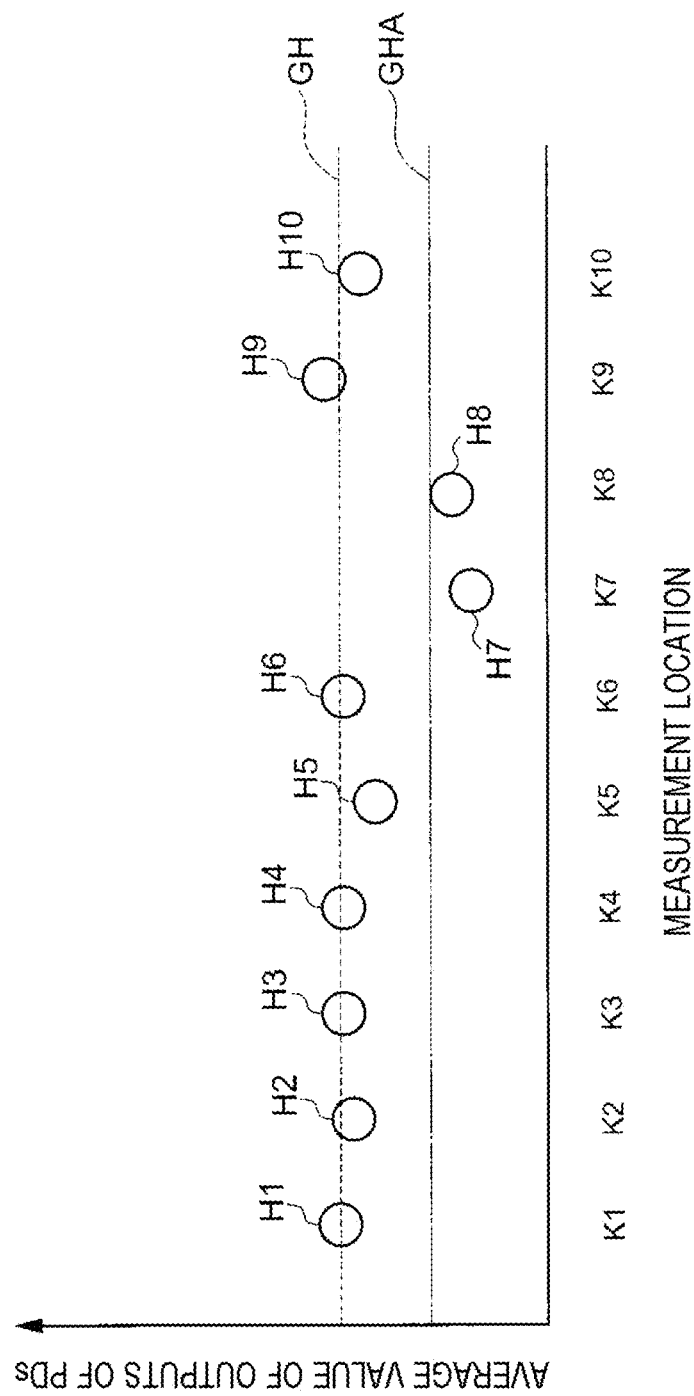
FIG. 22 is a graph for explaining an inspection for Abnormality C in a second inspection.

Similarly to the inspection for Abnormality B in the first inspection, as illustrated in FIG. 22, the average value of the output values of the plural light receiving elements 16 (see FIG. 10) is obtained for each of the inspection locations K (see FIG. 9) of the surface 200 of the object OB, and the median value GH of the average values H1 to H10 of the plural inspection locations K is obtained. The median value GH of the average values H1 to H10 is set to the reference value. Further, whether each inspection location K is "Normality" or "Abnormality B" is inspected using the average values H1 to H10 of the respective inspection locations K and the reference value (median value) GH.

Here, a case where the inspection location K7 and the inspection location K8 are Abnormality C as illustrated in FIG. 22 will be described.

In the inspection locations K1 to K6, K9, and K10 other than the inspection locations K7 and K8, as illustrated in FIG. 15, a large number of diffuse reflection components of the reflected light RF are not directed toward the opening 42. Thus, the light amount, which is received by the respective light receiving elements 16 disposed at the positions other than the opening 42 (position Cc), is large. Therefore, the average values H1 to H6, H9, and H10 of the plural light receiving elements 16 are large.

In contrast, as illustrated in FIG. 12, the specularly reflected light of the reflected light RF from the inspection locations K7 and K8 is directed toward the opening 42. No light receiving element 16 is provided at the position Cc where the peak P of the light beam is present. Further, since a large amount of specular reflection components of the reflected light RF is directed toward the opening 42, the light amount, which is received by the respective light receiving elements 16 disposed at positions other than the position of the opening 42 (position Cc), is small. Therefore, the average values H7 and H8 of the output values of the plural light receiving elements 16 are small.

Therefore, as illustrated in the graph in FIG. 22, the average values H7 and H8 in the inspection locations K7 and K8 protrude and decrease. Further, the controller 20 determines whether the inspection location K is "Normality" or "Abnormality C," the reference value (median value) GH and the average values H1 to H10.

For example, in a case where a difference between the reference value (median value) GH and each of the average values H1 to H10 is out of the predetermined range, the inspection location K is determined as "Abnormality C". Alternatively, a threshold value GHA is set by performing the four arithmetical operations on the reference value GH with a predetermined value, and the inspection location K having the average values H1 to H10 which are below the threshold value GHA is determined as "Abnormality C".

[Abnormality D]

Figure 23:
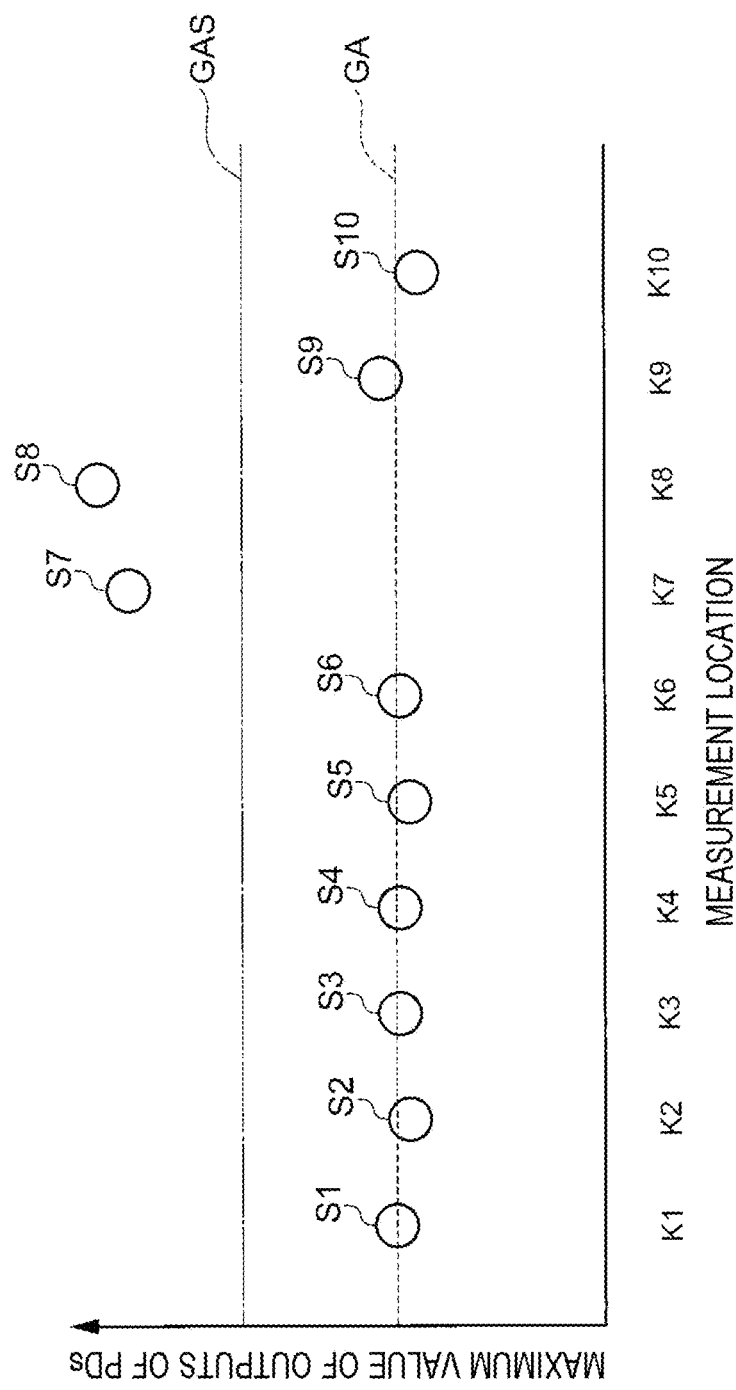
FIG. 23 is a graph for explaining an inspection for Abnormality D in the second inspection.

Similarly to the inspection for Abnormality A in the first inspection, as illustrated in FIG. 23, a largest value, that is, a maximum value is obtained among output values of the plural light receiving elements 16 (see FIG. 10) for each inspection location K (see FIG. 9) of the surface 200 of the object OB. Next, a median value GA of the maximum values S1 to S10 of the plural inspection locations K is obtained, and the median value GS of the maximum values S1 to S10 is set to a reference value. Further, whether each inspection location K is "Normality" or "Abnormality D" is inspected using the maximum values S1 to S10 of the respective inspection locations K and the reference value (median value) GS.

Here, a case where the inspection location K7 and the inspection location K8 are Abnormality D as illustrated in FIG. 23 will be described.

In the inspection locations K1 to K6, K9, and K10 other than the inspection locations K7 and K8, as illustrated in FIG. 15, the light amount of the peak P of the light amount of the diffuse reflection component of the reflected light RF, which is not directed toward the opening 42, is small. Thus, the maximum value of the plural light receiving elements 16 is small.

In contrast, as illustrated in FIG. 13, much of specularly reflected light of the reflected light RF from the inspection locations K7 and K8 is not directed toward the opening 42. As a result, the peak P in the light amount of the light beam is received by the light receiving element Cb. Therefore, the maximum value of the plural light receiving elements 16 (in this example, the output value of the light receiving element 16Cb) is large.

Therefore, as illustrated in the graph in FIG. 23, the maximum values S7 and S8 in the inspection locations K7 and K8 protrude and increase. Further, the controller 20 determines whether the inspection location K is "Normality"

or "Abnormality D," using the reference value (median value) GS and the maximum values S1 to S10.

For example, in a case where a difference between the reference value (median value) GS and each of the maximum values S1 to S10 is out of the predetermined range, the inspection location K is determined as "Abnormality D". Alternatively, a threshold value GSA is set by performing the four arithmetical operations on the reference value GS with a predetermined value, and the inspection location K having the maximum values S1 to S10 which exceed the threshold value GSA is determined as "Abnormality D".

Here, similarly to the first inspection, in a case where the specularly reflected light of the reflected light RF from the inspection location K which is "Abnormality D" and which is on the surface 200 of the object OB is directed toward a portion other than the opening 42, an output values of the light receiving element 16 which is disposed at a position of the peak P of the specularly reflected light from the inspection location K or output values of the light receiving element 16 in interest and the light receiving elements 16 at the periphery thereof are not used.

In a case where the direction of the specularly reflected light of the reflected light RF from each of the inspection locations K is a line shape instead of a dot shape, like the first inspection, an output value of the corresponding light receiving element 16 or output values of the corresponding light receiving element 16 and the light receiving elements 16 at the peripheral thereof are not used.

(Third Inspection)

Next, a third inspection for inspecting the reflection characteristics of the respective inspection locations K on the surface 200 of the object OB will be described.

Figure 16:
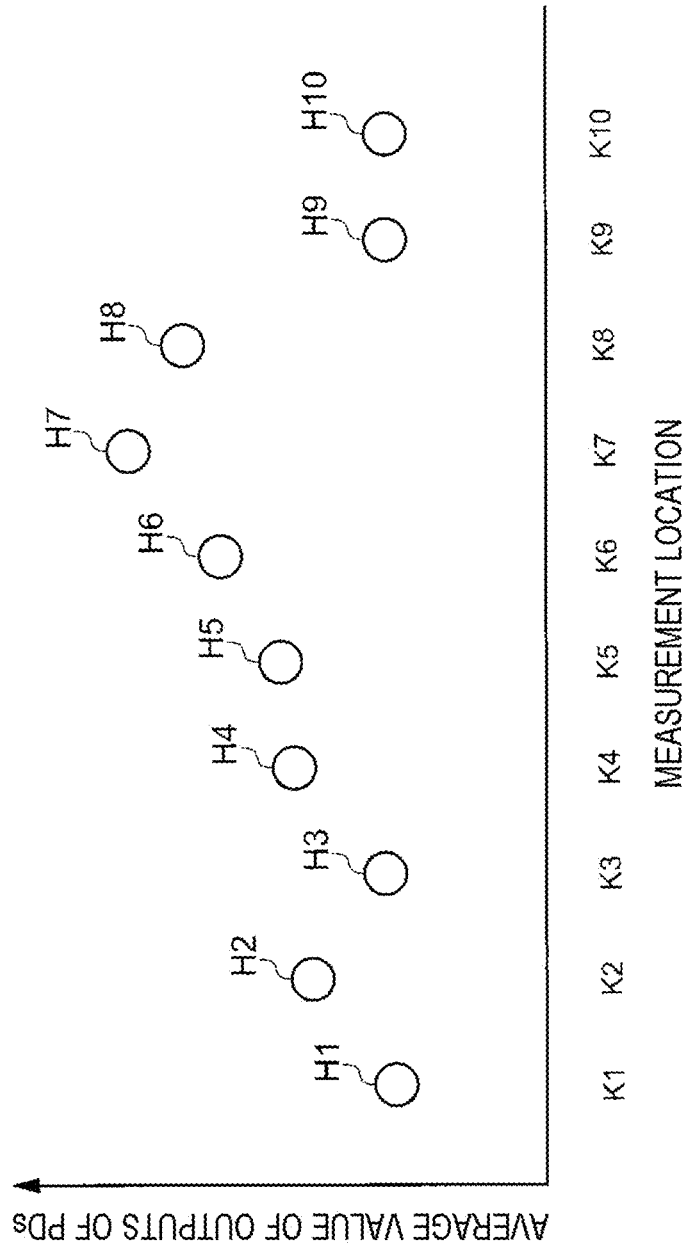
FIG. 16 is a graph for explaining a magnitude of an average value of a light amount of the diffuse reflection light.

The controller 20 determines the roughness level (the number of diffuse reflection components) of each inspection location K, using the average value H used for the first inspection. For example, as illustrated in FIG. 16, the roughness level (the number of diffuse reflection components) is determined using an average value H of each of the inspection locations K without obtaining the median value GS (see FIG. 14).

[Others]

In the descriptions of the first inspection and the second inspection, the median value (reference value) GS of the maximum values S and the median value (reference value) GH of the average values H are obtained from the output values of the plural light receiving elements 16 of all of the inspection locations K of the surface 200 of the object OB, but the present invention is not limited thereto. A part of all of the inspection locations K may be used. In addition, in a case where a part of all of the inspection locations K is used, only the inspection location K which is "Normality" may be used, but of the plural normal inspection locations K which is "Normality" may be included (e.g., 80% or more).

Further, in the aforementioned description, the median value (reference value) GS of the maximum values S and the median value (reference value) GH of the average values H are obtained using the object OB to be inspected, but the present invention is not limited thereto. The median value (reference value) GS of the maximum values S and the median value (reference value) GH of the average values H may be inspected using another object OB regardless of the object to be inspected, and the values may be stored in advance in the controller 20.

Figure 20:
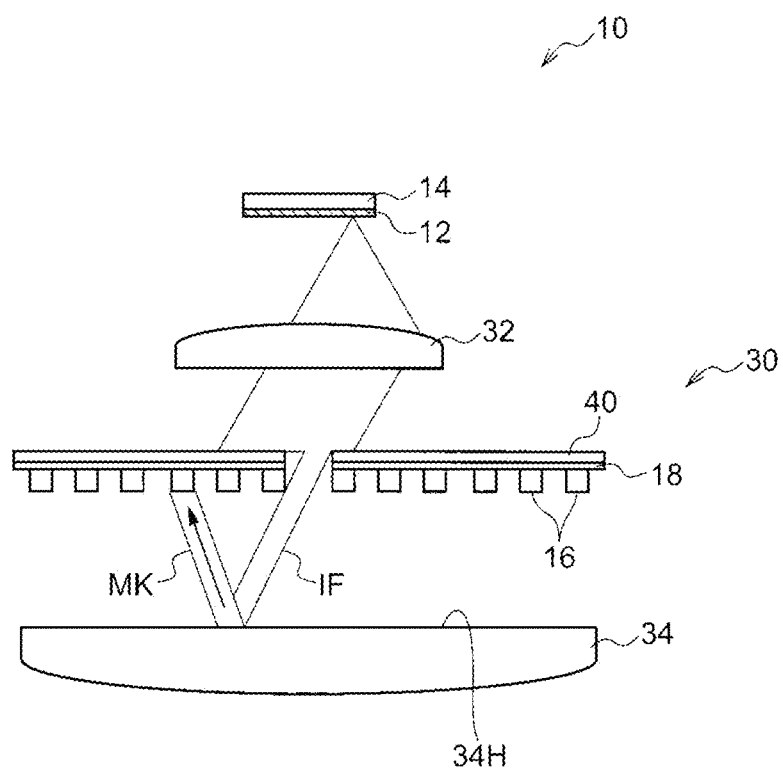
FIG. 20 is an explanatory view illustrating an example of reflected stray light in a case where a lens surface is a flat surface.
Figure 21:
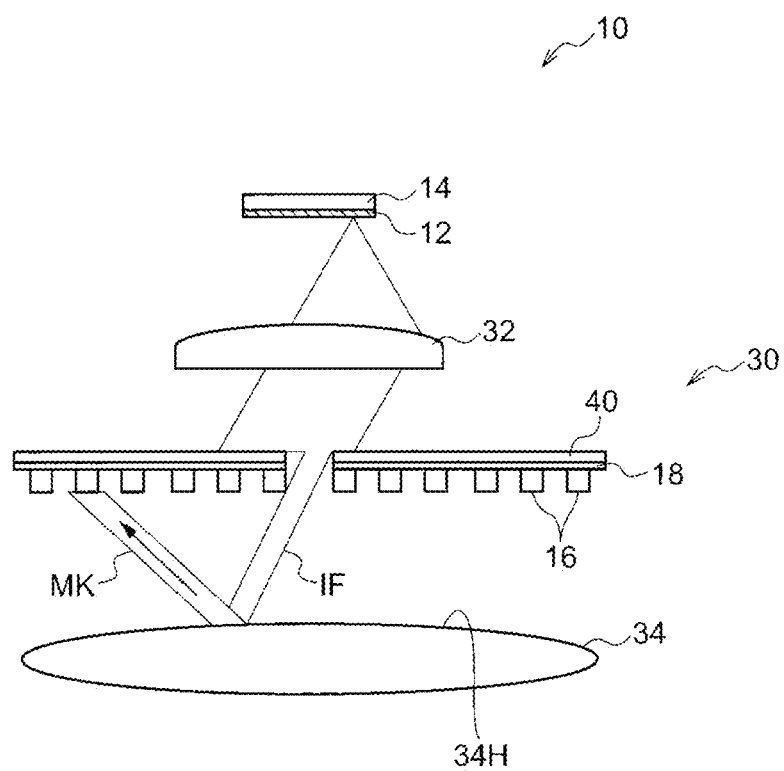
FIG. 21 is an explanatory view illustrating an example of reflected stray light in a case where a lens surface is a curved surface.

Further, anti-reflective coating is performed on the lens surface, but even in this case, it is impossible to remove reflected stray light reflected by a lens surface, and as a result, it is necessary to consider a countermeasure. For example, as illustrated in FIG. 20, the reflected stray light MK reflected by an upper surface 34H of the second lens 34 may be incident on the light receiving element 16 in some instances. In addition, even in a case where the upper surface 34H of the second lens 34 is a flat surface as illustrated in FIG. 20, and even in a case where the upper surface 34H is a curved surface as illustrated in FIG. 21, the reflected stray light MK may be incident on the light receiving element 16 in some instances.

Therefore, the light receiving element 16 on which the reflected stray light MK is incident is specified in advance through experiments or the like, and the light receiving element 16 on which the reflected stray light MK is incident is not used.

Similarly, in a case where stray light MK other than the reflected stray light MK is present, an output of the light receiving element 16 on which the stray light MK is incident is not used.

The light receiving element 16 on which the reflected stray light MK and other stray light are incident may not be installed. In addition, felt or an anti-reflective structure such as coating may be provided at the position where the light receiving element 16 is not installed.

<Operation>

Next, an operation of the present exemplary embodiment will be described.

By using the light receiving result (the maximum value and the average value) of the light receiving unit 18 for each of the inspection locations K1 to K10, and the median value, it is possible to easily and accurately inspect whether each inspection location K is in "a state where the light amount (specular reflection component) of the specularly reflected light of the reflected light is large", "a state where the direction of the specular reflection is changed", or "a state where the light amount (diffuse reflection component) of the diffuse reflection light of the reflected light is large", in comparison with a case where the light receiving result (the maximum value and the average value) and the median value are not used.

Further, by inspecting the inspection locations K using the average values of the light receiving unit 18 for the respective inspection locations K1 to K10, it is possible to easily and accurately inspect the magnitude of the light amount (diffuse reflection component) of the diffuse reflection light of the reflected light from the inspection locations K, that is, the roughness levels of the inspection locations K.

Further, an output of the light receiving element 16, in the light receiving unit 18, provided at a location which the specularly reflected light of the reflected light RF reflected by the object OB reaches is not used or no light receiving element 16 is provide at such a location. As a result, it is possible to accurately inspect the respective inspection locations K in comparison with a case where the output of the light receiving element 16 provided at such a location is used.

Further, an output of the light receiving element 16, in the light receiving unit 18, provided at a location which the stray light other than the reflected light RF reflected by the surface 200 of the object OB reaches is not used or no light receiving element 16 is provided at such a location. As a result, it is possible to accurately inspect the respective inspection locations K in comparison with a case where the output of the light receiving element 16 provided at the location is used.

[Others]

The present invention is not limited to the exemplary embodiment.

Figure 24:
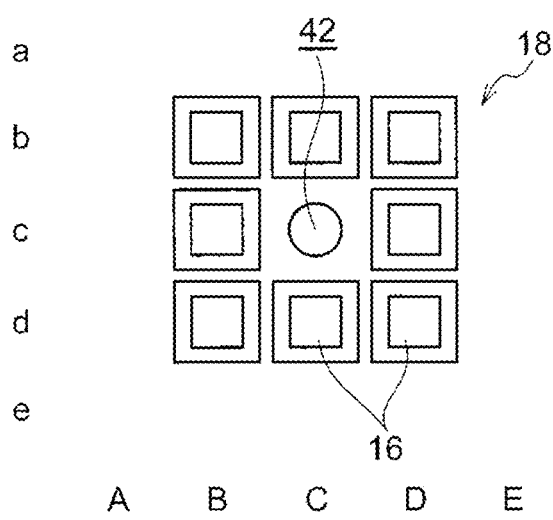
FIG. 24 is a top plan view of the light receiving unit, which illustrates another example of the arrangement of the light receiving elements.

For example, in the exemplary embodiment, the arrangement and the number of light receiving elements 16 in the light receiving unit 18 are illustrative, and the present invention is not limited thereto. For example, as illustrated in FIG. 24, eight light receiving elements 16 may be provided. In addition, the light receiving elements 16 may not be disposed around the opening 42, and the opening 42 may be disposed at an end portion.

Further, in the present exemplary embodiment, as illustrated in FIG. 1, the light receiving elements 16 are disposed at an optical axis M side (at an inner side) of the virtual line P (cylindrical surface) in the width direction of the apparatus. The virtual line P extends in the up and down direction of the apparatus while passing through an outer diameter end (a virtual contact point between a front surface Rd (radius) and a back surface Rd) of one lens (in the present exemplary embodiment, the second lens 34) having a larger outer diameter than the other lens (in the present exemplary embodiment, the first lens 32) has. It should be noted that the present invention is not limited thereto. The light receiving element 16 may be disposed outside the virtual line P.

Further, in the exemplary embodiment, the "median value" of the maximum values or the average values of the outputs of the respective light receiving elements 16 is set to the reference value, and the threshold value is set based on the reference value (median value). However, the present invention is not limited thereto. For example, an "average value" of the maximum values or the average values of all of the inspection locations may be set to the reference value. Alternatively, the reference value may be a value other than the "median value" or the "average value". In addition, a value other than the maximum value or the average value of outputs of the light receiving elements 16 may be used.

Further, the present invention is not limited to the configurations of the exemplary embodiment and may be implemented in various configurations. In addition, it is evident that the present invention may be carried out in various aspects without departing from the subject matter of the present invention.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. An inspection apparatus comprising:
a light emitting unit that emits irradiation light to an object to be inspected;
a first lens that changes a divergence level of the irradiation light which is emitted from the light emitting unit and is transmitted through the first lens;
an aperture unit that has an opening which narrows the irradiation light transmitted through the first lens;
a second lens that condenses the irradiation light passing through the opening, toward the object;
a light receiving unit that is disposed between the aperture unit and the second lens, and that includes a plurality of light receiving elements which receives reflected light obtained by the irradiation light being emitted to the object and then being transmitted through the second lens, the plurality of light receiving elements being disposed so as not to overlap the opening; and
an inspection unit that inspects respective inspection locations of the object using (i) light receiving results of the light receiving unit for the respective inspection locations of the object and (ii) a reference value.

2. The inspection apparatus according to claim 1, wherein the reference value is set based on a median value of the light receiving results of the plurality of inspection locations.

3. The inspection apparatus according to claim 1, wherein the light receiving result is a maximum value of output values of the plurality of light receiving elements of the light receiving unit for each inspection location.

4. The inspection apparatus according to claim 2, wherein the light receiving result is a maximum value of output values of the plurality of light receiving elements of the light receiving unit for each inspection location.

5. The inspection apparatus according to claim 1, wherein the light receiving result is an average value of output values of the plurality of light receiving elements of the light receiving unit for each inspection location.

6. The inspection apparatus according to claim 2, wherein the light receiving result is an average value of output values of the plurality of light receiving elements of the light receiving unit for each inspection location.

7. An inspection apparatus comprising:
a light emitting unit that emits irradiation light to an object to be inspected;
a first lens that changes a divergence level of the irradiation light which is emitted from the light emitting unit and is transmitted through the first lens;
an aperture unit that has an opening which narrows the irradiation light transmitted through the first lens;
a second lens that condenses the irradiation light passing through the opening, toward the object;
a light receiving unit that is disposed between the aperture unit and the second lens, and that includes a plurality of light receiving elements which receives reflected light obtained by the irradiation light being emitted to the object and then being transmitted through the second lens, the plurality of light receiving elements being disposed so as not to overlap the opening; and
an inspection unit that inspects reflection characteristics of respective inspection locations of the object using an average value of output values of the light receiving unit for the respective inspection location.

8. The inspection apparatus according to claim 1, wherein a light receiving element provided at a location in the light receiving unit on which specularly reflected light of the reflected light reflected by the object is incident is not used.

9. The inspection apparatus according to claim 2, wherein a light receiving element provided at a location in the light receiving unit on which specularly reflected light of the reflected light reflected by the object is incident is not used.

10. The inspection apparatus according to claim 3, wherein a light receiving element provided at a location in the light receiving unit on which specularly reflected light of the reflected light reflected by the object is incident is not used.

11. The inspection apparatus according to claim 4, wherein a light receiving element provided at a location in the light receiving unit on which specularly reflected light of the reflected light reflected by the object is incident is not used.

12. The inspection apparatus according to claim 5, wherein a light receiving element provided at a location in the light receiving unit on which specularly reflected light of the reflected light reflected by the object is incident is not used.

13. The inspection apparatus according to claim 6, wherein a light receiving element provided at a location in the light receiving unit on which specularly reflected light of the reflected light reflected by the object is incident is not used.

14. The inspection apparatus according to claim 7, wherein a light receiving element provided at a location in the light receiving unit on which specularly reflected light of the reflected light reflected by the object is incident is not used.

15. The inspection apparatus according to claim 1, wherein a light receiving element at a location of the light receiving unit on which stray light other than the reflected light reflected by the object is incident is not used.

16. The inspection apparatus according to claim 2, wherein a light receiving element at a location of the light receiving unit on which stray light other than the reflected light reflected by the object is incident is not used.

17. The inspection apparatus according to claim 3, wherein a light receiving element at a location of the light receiving unit on which stray light other than the reflected light reflected by the object is incident is not used.

18. The inspection apparatus according to claim 5, wherein a light receiving element at a location of the light receiving unit on which stray light other than the reflected light reflected by the object is incident is not used.

19. The inspection apparatus according to claim 7, wherein a light receiving element at a location of the light receiving unit on which stray light other than the reflected light reflected by the object is incident is not used.

20. The inspection apparatus according to claim 8, wherein a light receiving element at a location of the light receiving unit on which stray light other than the reflected light reflected by the object is incident is not used.

\* \* \* \* \*